US011826441B2

(12) United States Patent
Sun et al.

(10) Patent No.: US 11,826,441 B2
(45) Date of Patent: Nov. 28, 2023

(54) CLEANSING FOAM COSMETIC COMPOSITION COMPRISING AMINO ACID-BASED SURFACTANTS

(71) Applicants: Kolmar Korea Co., Ltd., Sejong-si (KR); SHINSEGAE INTERNATIONAL INC., Seoul (KR)

(72) Inventors: Yan Sun, Seoul (KR); Min Kyung Kim, Seoul (KR); Young Seok Kim, Seoul (KR); Yi Soo Bae, Seoul (KR); Jun Oh Kim, Yongin-si (KR); Sang Keun Han, Seoul (KR); So Yoon Baek, Seoul (KR); Kang Tae Lee, Seoul (KR); So Hyeon Mok, Seoul (KR)

(73) Assignees: KOLMAR KOREA CO., LTD., Sejong-si (KR); SHINSEGAE INTERNATIONAL INC., Seoul (KR)

( * ) Notice: Subject to any disclaimer, the term of this patent is extended or adjusted under 35 U.S.C. 154(b) by 0 days.

(21) Appl. No.: 17/848,245

(22) Filed: Jun. 23, 2022

(65) Prior Publication Data

US 2023/0000732 A1 Jan. 5, 2023

(30) Foreign Application Priority Data

Jul. 2, 2021 (KR) ........................ 10-2021-0087318

(51) Int. Cl.
*A61Q 19/00* (2006.01)
*A61K 8/04* (2006.01)
*A61K 8/44* (2006.01)

(52) U.S. Cl.
CPC ................ *A61K 8/046* (2013.01); *A61K 8/44* (2013.01); *A61Q 19/00* (2013.01); *A61K 2800/30* (2013.01); *A61K 2800/522* (2013.01); *A61K 2800/596* (2013.01)

(58) Field of Classification Search
None
See application file for complete search history.

(56) References Cited

U.S. PATENT DOCUMENTS

2017/0360672 A1\* 12/2017 Maka ....................... C11D 1/83

FOREIGN PATENT DOCUMENTS

| CN | 105902411 | | 8/2016 |
| CN | 110151578 | A | 8/2019 |
| KR | 101042717 | | 6/2011 |
| KR | 20170058146 | | 5/2017 |
| KR | 20190090841 | | 8/2019 |
| WO | 2017106276 | | 6/2017 |
| WO | 2018225096 | | 12/2018 |

OTHER PUBLICATIONS

AHC French Spa Green Mud Cleanser retrieved on Jan. 14, 2021 from https://blog.naver.com/vvv_00_vvv/222207477196.
Korean Office Action—Korean Application No. 10-2021-0087318 dated Sep. 6, 2021, citing AHC French Spa Green Mud Cleanser and WO 2018/225096.
Chinese Office Action—Chinese Application No. 202111190822.7 dated Jul. 29, 2023, citing CN 110151578.

\* cited by examiner

*Primary Examiner* — Brian Gulledge
(74) *Attorney, Agent, or Firm* — CANTOR COLBURN LLP

(57) ABSTRACT

Provided is a cleansing foam cosmetic composition comprising amino acid-based surfactants, and more particularly to a cleansing foam cosmetic composition in which a nonionic or amphiprotic surfactant is not used, and which comprises amino acid-based surfactants consisting of only sodium lauroyl glutamate, sodium cocoyl glycinate, and potassium cocoyl glycinate.

12 Claims, 3 Drawing Sheets

CLEANSING FOAM COSMETIC COMPOSITION COMPRISING AMINO ACID-BASED SURFACTANTS

BACKGROUND OF THE INVENTION

Field of the Invention

The present invention relates to a cleansing foam cosmetic composition comprising amino acid-based surfactants, and more particularly to a cleansing foam cosmetic composition in which a nonionic or ionic surfactant is not used, and which comprises amino acid-based surfactants consisting of only sodium lauroyl glutamate, sodium cocoyl glycinate, and potassium cocoyl glycinate.

Description of the Related Arts

In general, a cleansing agent is a general cosmetic used for cleanliness of the skin, and functions to maintain a skin state moistly and healthfully by removing sweat or sebum on a surface of the skin, various wastes, such as dust, aged horny substance, and so on, residual substance resulting from a makeup, and other pollutants.

Soap is frequently used as a cleansing agent for mainly washing the skin. However, the soap is strongly alkaline showing a pH value of about 9 to 10, and may give stimulation to a weak skin. Also, because most soap contains a small quantity of skin moisture element, and is made only for showing complete cleansing ability, when it is used in a dry skin, dehydration of the skin, or roughness of the skin may be shown.

Cleansing foam is intended for making up for the disadvantages of this general soap. Thus, the cleansing foam has mainly been developed for washing of a sensitive skin, such as a face, so it almost has a low pH value (mainly neutrality or weak acidity) and contains a moisture element.

Existing surfactants which have been used consist mostly of petroleum-based surfactants produced through several times of processes after extraction of crude oil, and these petroleum-based surfactants have been known as causing the problem of environmental pollution and the problem of stability on the human body. That is, if they are absorbed into the skin, a skin protection membrane may be damaged, and an itch or dermatitis may be generated, and if they are repeatedly used in the skin for a long time, the loss of hair, an allergy, a decline in immunity from atopy, and so on may be caused. Accordingly, due to these problems, studies for developing eco-friendly bio-surfactants to substitute for the petroleum-based surfactants tends to have actively been carried out. Although the biosurfactants have been defined as surface activity biomolecules having their wide application scopes, and generated by microorganisms, they have recently been defined as including all the surfactants produced using renewable natural vegetable materials.

Amino acids have often been used in synthesis of surfactants because they have excellent biodegradability, and surface activity capable of efficiently lowering interfacial energy, and amino acid-based surfactants synthesized using amino acids are advantageous in that they have excellent biocompatibility, multi-functionality, nontoxic and nonirritant properties, don't harm underwater life, and have excellent biodegradability. Furthermore, many amino acid-based surfactants comprising n-acyl amino acid based-surfactants have also been known as having sterilizing power against microorganisms causing diseases.

However, it has been reported that each of the amino acid-surfactants basically has two functional groups, an amine group and a carboxyl group, and because these amino acid-based compounds have low reactivity to a high-quality fatty or high-class alcohol, a large quantity of non-reactant remains. Furthermore, because an additional process is required for removing a non-reactive fatty acid, the amino acid-surfactants aren't advantageous economically largely. Thus, methods of synthesizing amino acid-based anionic biosurfactants using raw materials originating from nature, such as coconut oil, and so on have been studied.

Meanwhile, although general amino acid-based surfactants have the advantages of softly reacting to the skin and having excellent biodegradability, they are also disadvantageous in that foaming ability causing foam, or cleansing ability to remove pollutants is not sufficient.

In order to solve this disadvantage of being inferior in cleansing ability, there were many studies intended for using various amino acid-surfactants in a state of being mixed with synthetic surfactants or amphiprotic surfactants, and so on (Patent Documents 1 to 5 below). According to circumstances, bubbling ability (foaming ability), washing ability (rinse property), or the like varies according to each mixed ratio of the surfactants.

In addition to these surfactants, nonionic surfactants may further be used for realizing solubilization and emulsification dispersion functions.

In general, when surfactants having different properties are used in a state of being mixed, their disadvantages are supplemented more than when only one kind of surfactant is used, and thus although there are partly utilized study methods, it is difficult to solve eco-friendly problems under an aspect.

Accordingly, it has been required to develop a new cleansing foam cosmetic composition, foaming ability or cleansing ability of which doesn't decline, although surfactants of being soft while being low irritant to the skin, and having excellent biodegradability are used therein.

PRIOR ART DOCUMENTS

Patent Documents (Patent Document 1) Korean Patent No. 10-1042717 (registered on Jun. 13, 2011)
(Patent Document 2) Korean Laid-Open Patent Publication No. 10-2017-0058146 (published on May 26, 2017)
(Patent Document 3) Korean Laid-Open Patent Publication No. 10-2019-0090841 (published on Aug. 2, 2019)
(Patent Document 4) International Patent Publication No. WO 2017/106276 (published on Jun. 22, 2017)
(Patent Document 5) Chinese Laid-Open Patent Publication No. CN 105902411 A (published on Aug. 31, 2016)

Non-Patent Document (Non-Patent Document 1) Da Nan Yea, and al., 'Study on Synthesis of Amino-Acid based Anionic Surfactants from Coconut Oil, and Characterization of Interfacial Properties', Appl. Chem. Eng., Vol. 29, No. 5, October 2018, 524-532.

SUMMARY OF THE INVENTION

The present invention has been devised for solving the problems, and an object of the present invention is to provide a cleansing foam cosmetic composition that doesn't give stimulation to the skin and has a mild feeling of use.

Furthermore, another object of the present invention is to provide a cleansing foam cosmetic composition that does not comprise ionic or nonionic surfactants at all, but can maintain cleansing ability, foaming ability, and foam maintenance ability using only amino acid-based surfactants which are eco-friendly biosurfactants.

In order to achieve the objects, a cleansing foam cosmetic composition according to the present invention may comprise amino acid-based surfactants consisting of: (A) sodium lauroyl glutamate; (B) sodium cocoyl glycinate; and (C) potassium cocoyl glycinate.

7 to 25 wt % of said (A) sodium lauroyl glutamate, 7 to 25 wt % of said (B) sodium cocoyl glycinate, and 1 to 5 wt % of said (C) potassium cocoyl glycinate with respect to a total weight of the cleansing foam cosmetic composition may be included.

A weight ratio of (A) sodium lauroyl glutamate, (B) sodium cocoyl glycinate, and (C) potassium cocoyl Glycinate included in the cleaning foam cosmetic composition may be 10:10:1.4. If necessary, the weight ratio may be selected within the range of 7:7:1 to 13:13:1.4.

The cleansing foam cosmetic composition may further comprise water, an antioxidant, and a moisturizing agent.

As described above, the cleansing foam cosmetic composition according to one exemplary embodiment of the present invention doesn't give stimulation to the skin, and is excellent because it provides a mild feeling of use even after use.

Furthermore, according to the present invention, it is characteristic in that biodegradability is excellent because only friendly-environmental amino acid-based surfactants are used, and cleansing ability, foaming ability, and foam maintenance ability are also excellent.

DETAILED DESCRIPTION OF THE INVENTION

Figure 1:
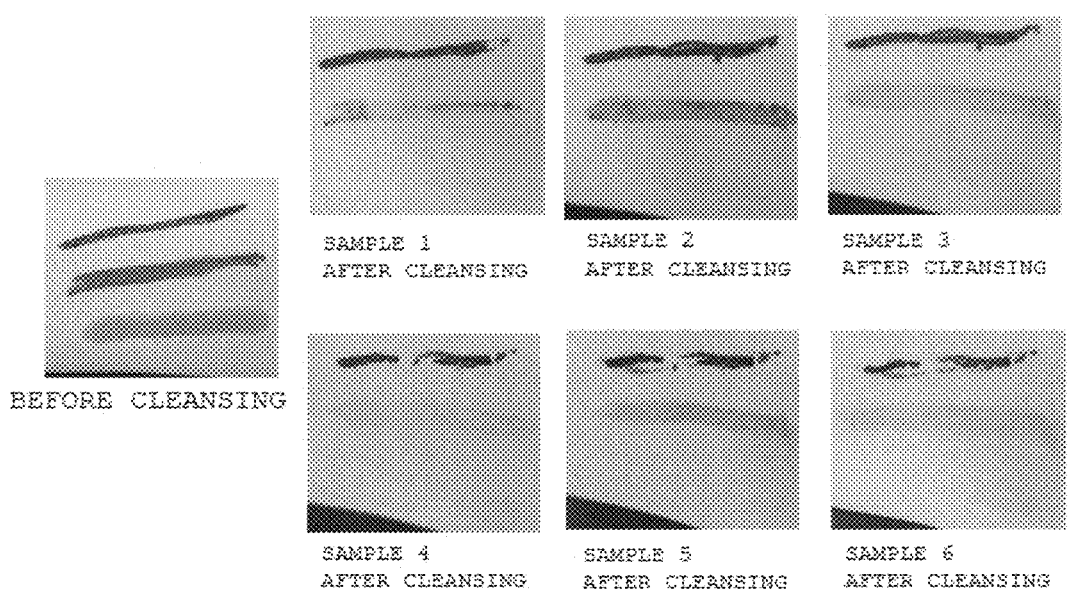
FIG. 1 represents pictures for comparing cleansing abilities shown in the cases in which three kinds of amino acid-based surfactants are used independently, and in a mixed state.

It should be apparent that the present invention may be embodied in various forms, various modifications can be made, and the present invention is described on the basis of specific exemplary embodiments. However, the present invention should not be construed as being limited to the specifically disclosed exemplary embodiments, but should be understood as comprising all modifications, equivalents or alternations included in the idea and technical scope of the present invention.

Furthermore, the terms used in the present specification are only used for describing the specific exemplary embodiments, and are not intended for limiting the present invention. It should be understood that all the terms used herein including technical or scientific terms have the same meanings as those which are generally understood by those having ordinary skill in the art field to which the present invention pertains, unless they are defined differently.

The inventors of the present invention made studies and efforts in order to get over the problems of the conventional arts, and as a result thereof, in the case of cleansing foam produced by mixing of only specific kinds of amino acid-based surfactants, it was found that the cleansing foam is low irritant to the skin, is friendly environmental, and also has excellent properties with respect to cleansing ability, foaming ability, and foam maintenance ability, and so on.

As the ingredients of amino acid-based anionic surfactants penetrate into between the scalp, which is a surface targeted for cleansing, and the hair, the adhesive power of wastes becomes weakened so that cleansing can easily be performed by physical power. The appropriate cleansing property and foaming ability of these anionic surfactants act as important elements for removing wastes from the scalp and the hair.

In general, although the amino acid-based surfactants have widely been known as representative surfactants for producing a hypoallergenic cleansing agent, and have also been known as having good biodegradability, it is problematic in that the cleansing agent does not foam well, slipperiness and stickiness often remain even after cleaning, and the cost of production rises.

The amino acid-based surfactants preferable to be used in the cleansing foam cosmetic composition according to the present invention may appropriately be selected and used according to each purpose, and for example, surfactants based on amino acids of being acidic, such as N-acyl glutamates, and surfactants based on amino acids of alkalescency verging on neutrality shown in acyl glycinates can all be used.

In particular, it is preferable to select sodium lauroyl glutamate, sodium cocoyl glycinate, and potassium cocoyl glycinate which are obtainable from natural raw materials.

The sodium lauroyl glutamate is obtainable from coconut oil or palm oil, and so on, and is an anionic surfactant ingredient originating from glutamic (amino acid), lauric acid, and natrium. It is a vegetable ingredient which may substitute for a synthetic surfactant and is characteristic in that biodegradability is excellent. Furthermore, because the sodium lauroyl glutamate acts as an active material so as to be mixed well by being absorbed into surfaces of each materials, it helps to stabilize constituent ingredients which are not mixed in a cosmetic. In particular, it can widely be utilized as a cleansing ingredient showing the same weak acidity as pH of the skin, and can provide an excellent feeling of use because it causes cleansing to be finished by a soft feeling of touch.

The sodium cocoyl glycinate and the potassium cocoyl glycinate are anionic surfactants based on a vegetable amino acid extracted from coconut fruit having a pH value of 8 to 9, have biodegradability as ingredients originating from nature, are not almost give stimulation to the skin, and are safe. Because foam generation ability is excellent, they can cause cleansing to be softly performed, and they can also cause soft foam, and provide high cleansing ability and a moisture use sensation.

Accordingly, when the three ingredients are appropriately mixed, high skin stability can be realized, a feeling of use can also be improved, and a mild cleansing foam cosmetic composition having an excellent cleansing or foam effect more than ever can be realized.

According to a preferable embodiment of the present invention, each of the amino acid-based anionic surfactants has a content which ranges from 15 to 30 wt % with respect to a whole composition. Preferably, the content may be used in the range of 20 to 25 wt %. When the respective contents of the amino acid-based anionic surfactants are less than 15 wt %, it is problematic in that the elasticity of foam lacks, or ability of relieving stimulation to the skin decreases, and when their respective contents are more than 30 wt %, it is problematic in that a feeling of use is not good because hardness becomes higher.

7 to 25 wt % of (A) sodium lauroyl glutamate, 7 to 25 wt % of (B) sodium cocoyl glycinate, and 1 to 5 wt % of (C) potassium cocoyl glycinate with respect to a total weight of the cleansing foam cosmetic composition are included. It is the most preferable that a weight ratio (A:B:C) of the amino acid-based surfactants is 10:10:1.4. If necessary, the weight ratio of the ingredients may also be selected within the range of 7:7:1 to 13:13:1.4.

In the cleansing foam cosmetic composition according to the present invention, in addition to the aforesaid essential ingredients, ingredients used in general cosmetics, such as remaining purified water, an antioxidant, a cosmetic preparation, a moisturizing agent, a ultraviolet ray absorbent, a perfume, and so on may be mixed within the scope which does not influence the effects of the present invention.

According to the present invention, polyvalent alcohol is included as a moisturizing agent for providing a moisture feeling after cleansing. For example, the polyvalent alcohol may be any one or more selected from the group consisting of glycerin, diglycerin, 1,3-butylene glycol, ethylene glycol, propylene glycol, Dipropylene glycol, sorbitol, maltitol, 1,2-pentanediol, and 1,2-hexanediol, but is not limited thereto.

A method of manufacturing the cleansing foam cosmetic composition according to the present invention is not specially limited, and a produced formulation shows a cream state or a paste state.

Hereinafter, the present invention is described in more detail on the basis of preferable examples.

EXAMPLES. INVESTIGATION ON PROPERTIES RESULTING FROM MIXING OF THE SURFACTANTS FOR PRODUCING THE CLEANSING FOAM COSMETIC COMPOSITION

Table 1 below shows each content ratio applied to the cases in which three kinds of amino acid-based surfactants are used independently, and in a mixed state. Cleaning ability, foaming ability, and foam maintenance ability aimed at each of Samples 1 to 6 were examined.

TABLE 1

Samples in which three kinds of amino acid-based surfactants are used independently, and in a mixed state

| Sample Nos. | 1 | 2 | 3 | 4 | 5 | 6 |
|---|---|---|---|---|---|---|
| D.I WATER | TO 100 | TO 100 | TO 100 | TO 100 | TO 100 | TO 100 |
| (A) SODIUM LAUROYL GLUTAMATE | 21.4 | — | — | 1.4 | 10 | 10 |
| (B) SODIUM COCOYL GLYCINATE | — | 21.4 | — | 10 | 10 | 1.4 |
| (C) POTASSIUM COCOYL GLYCINATE | — | — | 21.4 | 10 | 1.4 | 10 |

Experimental Example 1. Valuation on Cleansing Ability

The inside parts of the forearm of a human body were uniformly coated with the ingredients of waterproof mascara, waterproof eyebrow, and lipstick that are in deep colors and have high staying power in the representative size of 5 cm wide×1 cm deep, and were neglected for ten minutes, and then tests for cleansing ability were carried out with the six sample surfactants (21.4% sol). The inside parts of the forearm were scrubbed while circles were drawn around them thirty times under the pressure applied as much as the amount of about 10 ml, were then washed with lukewarm water and were dehydrated.

As a result thereof, as can be seen from FIG. 1, although the ingredient of the waterproof mascara wasn't almost completely erased, the respective ingredients of the waterproof eyebrow and the lipstick showed higher cleansing abilities when the mixed surfactants (Samples 4, 5 and 6) were used than when the surfactants were used independently (Samples 1, 2, and 3). In particular, the result of Sample 5 showed the most excellent washing ability.

Experimental Example 2. Valuation on Foaming Ability

Figure 2:
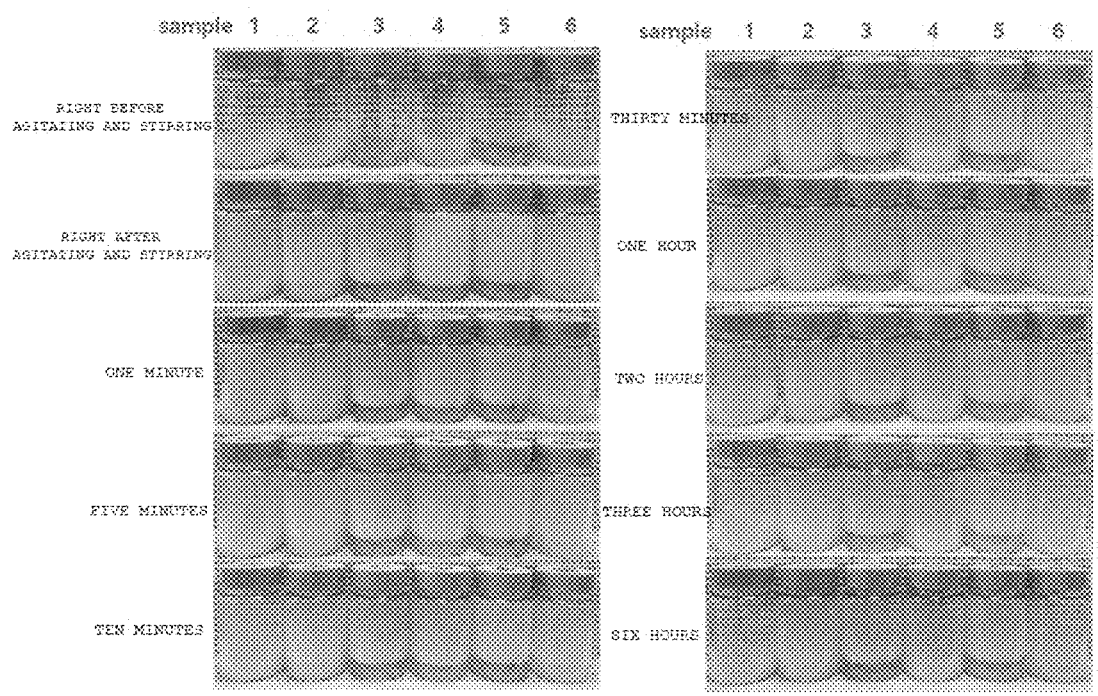
FIG. 2 represents pictures resulting from observing respective foam generation levels of the surfactants according to each time.

Concerning each of Samples 1 to 6 of the surfactants, 1% sol was put into a 100 vial vessel in the amount of 20 g, and was agitated and stirred up and down ten times, and then their respective foam generation levels were observed according to each time. As can be seen from FIG. 2, foaming abilities shown in Samples 4 and 5 were observed to be excellent.

Experimental Example 3. Valuation on Foam Maintenance Ability

Figure 3:
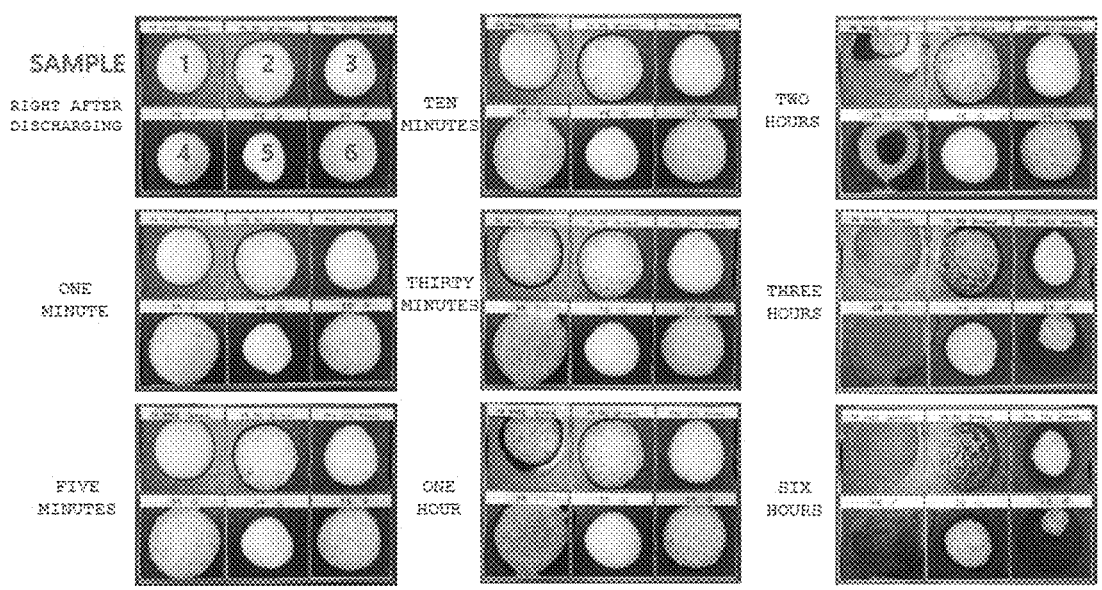
FIG. 3 represents pictures resulting from observing foam maintenance levels according to each time after discharging each of the surfactant.

Concerning each of Samples 1 to 6 of the surfactants, 1% sol was put into an auto-foam vessel in the amount of 20 g, was discharged identically three times, and then was observed according to each time. As can be seen from FIG. 3, foam was mostly maintained even after one hour, and particularly Samples 3 and 5 were observed as showing excellent foam maintenance ability.

Experimental Example 4. Test for Formulation

In order to look about whether a formulation is embodied or not according to each ratio of the surfactants, eight samples were prepared, and were compared with one another. In Examples 1 to 6 and Comparative Example 1 prepared on the basis of the results of the experimental examples, the surfactants of (A) sodium lauroyl glutamate, (B) sodium cocoyl glycinate, and (C) potassium cocoyl glycinate were mixed while being varied at fixed ratios.

In particular, in the case that a total amount of the three kinds of surfactants was in the range of 15 to 30 wt %, hardness was formed, and particularly when the total amount was in the range of 20 to 25 wt %, the most preferable hardness value could be obtained.

Although the potassium cocoyl glycinate among the surfactants was required to be maintained at the ratio of 1.4% or more, when its content became high relatively compared to those of the other two kinds of surfactants (corresponding to Comparative Example 1), it was problematic in the light of difficulty in its commercialization because viscosity of the surfactant deviated from the optimum range, and thus it was difficult to use the surfactant in a tube container.

Meanwhile, concerning Comparative Example 2 in which other ionic surfactants (sodium lauryl sulfate and cocamidopropyl betaine) in addition to the amino acid-based surfactants were additionally included and prepared, because hardness was too low, it was impossible to measure the hardness, and as a result of being confirmed through the measurement of viscosity instead of the hardness, it was measured that the viscosity was measured to be low (6,000 at 4*30 rpm, LV series viscometer).

That is, in the present invention, it could be confirmed that additionally mixing the surfactants having different properties acted as cutting desired effects in half rather than compensating for the disadvantages.

Here, a desired hardness of the formulation according to the present invention ranges from 50 to 300 N, preferably 50 to 100 N. The most preferable hardness ranges from 85 to 95 N.

TABLE 2

| INCI | Example 1 | Example 2 | Example 3 | Example 4 | Example 5 | Example 6 | Comparative Example 1 | Comparative Example 2 |
|---|---|---|---|---|---|---|---|---|
| WATER | 61.64 | 54.8 | 56.2 | 50.2 | 46.2 | 36.2 | 66.2 | 56.2 |
| HYDROXYACETOPHENONE | 0.5 | 0.5 | 0.5 | 0.5 | 0.5 | 0.5 | 0.5 | 0.5 |
| GLYCERIN | 20 | 20 | 20 | 20 | 20 | 20 | 20 | 20 |
| HYDROXYPROPYL STARCH PHOSPHATE | 0.5 | 0.5 | 0.5 | 0.5 | 0.5 | 0.5 | 0.5 | 0.5 |
| (A) SODIUM LAUROYL GLUTAMATE | 7 | 10 | 10 | 13 | 15 | 20 | 5 | 6.95 |
| (B) SODIUM COCOYL GLYCINATE | 7 | 10 | 10 | 13 | 15 | 20 | 5 | 6.95 |
| (C) POTASSIUM COCOYL GLYCINATE | 1.96 | 2.8 | 1.4 | 1.4 | 1.4 | 1.4 | 1.4 | 0.84 |
| SODIUM LAURYL SULFATE | — | — | — | — | — | — | — | 3.66 |
| COCAMIDOPROPYL BETAINE | — | — | — | — | — | — | — | 3 |
| 1,2-HEXANEDIOL | 1 | 1 | 1 | 1 | 1 | 1 | 1 | 1 |
| ETHYLHEXYLGLYCERIN | 0.3 | 0.3 | 0.3 | 0.3 | 0.3 | 0.3 | 0.3 | 0.3 |
| DECYLENE GLYCOL | 0.1 | 0.1 | 0.1 | 0.1 | 0.1 | 0.1 | 0.1 | 0.1 |
| RESULT | hardness of 15 | hardness of 35 | hardness of 91 | hardness of 110 | hardness of 250 | excess of harness | seperation | impossible to measure |

Experimental Example 5. Valuation on Skin Stimulation Property

Experiments aimed at fifteen panels for comparing skin stimulation properties shown after using the compositions of Example 3 and Comparative Example 2 were carried out. In the experiments for stimulation to the skin, after the back of the hand was coated with each composition, it was left for five minutes, and was cleansed and finished in water, and then in comparison of the feelings of stimulation which panels felt, each item concerning the properties of an itch, red spots, hives, tingle was marked out of 0 to 5 (the more the mark is high, the more stimulation properties are high), and the results thereof were then shown in Table 3 below.

Although skin stimulation indices of the two compositions weren't all high on the whole, it could be found that stimulation levels (particularly, the itch) shown in Example 3 in which only the amino acid-based surfactants were used were lots lower than those shown in Comparative Example 2 in which the ionic surfactants were additionally used.

TABLE 3

| Panel Nos. | Stimulation to the skin | Itch | Red spot | Hives | Tingle |
|---|---|---|---|---|---|
| 1 | Example 3 | 0 | 0 | 0 | 0 |
|   | Comparative Example 2 | 1 | 0 | 0 | 1 |
| 2 | Example 3 | 0 | 0 | 0 | 0 |
|   | Comparative Example 2 | 1 | 0 | 0 | 1 |
| 3 | Example 3 | 0 | 0 | 0 | 0 |
|   | Comparative Example 2 | 2 | 0 | 0 | 0 |
| 4 | Example 3 | 0 | 0 | 0 | 0 |
|   | Comparative Example 2 | 2 | 0 | 0 | 1 |

TABLE 3-continued

| Panel Nos. | Stimulation to the skin | Itch | Red spot | Hives | Tingle |
|---|---|---|---|---|---|
| 5 | Example 3 | 0 | 0 | 0 | 0 |
|   | Comparative Example 2 | 0 | 0 | 0 | 0 |
| 6 | Example 3 | 0 | 0 | 0 | 0 |
|   | Comparative Example 2 | 1 | 0 | 0 | 1 |
| 7 | Example 3 | 1 | 0 | 0 | 1 |
|   | Comparative Example 2 | 3 | 0 | 0 | 3 |
| 8 | Example 3 | 0 | 0 | 0 | 0 |
|   | Comparative Example 2 | 1 | 0 | 0 | 2 |
| 9 | Example 3 | 0 | 0 | 0 | 0 |
|   | Comparative Example 2 | 0 | 0 | 0 | 0 |

TABLE 3-continued

| Panel Nos. | Stimulation to the skin | Itch | Red spot | Hives | Tingle |
|---|---|---|---|---|---|
| 10 | Example 3 | 2 | 0 | 0 | 1 |
|  | Comparative Example 2 | 3 | 0 | 0 | 1 |
| 11 | Example 3 | 1 | 0 | 0 | 1 |
|  | Comparative Example 2 | 1 | 0 | 0 | 1 |
| 12 | Example 3 | 0 | 0 | 0 | 0 |
|  | Comparative Example 2 | 0 | 0 | 0 | 0 |
| 13 | Example 3 | 0 | 0 | 0 | 0 |
|  | Comparative Example 2 | 2 | 0 | 0 | 1 |
| 14 | Example 3 | 0 | 0 | 0 | 0 |
|  | Comparative Example 2 | 0 | 0 | 0 | 0 |
| 15 | Example 3 | 0 | 0 | 0 | 0 |
|  | Comparative Example 2 | 1 | 0 | 0 | 1 |

(Unit: wt %)

What is claimed is:

1. A cleansing foam cosmetic composition, comprising amino acid-based surfactants consisting of: (A) sodium lauroyl glutamate; (B) sodium cocoyl glycinate; and (C) potassium cocoyl glycinate.

2. The composition of claim 1, wherein 7 to 25 wt % of said (A) sodium lauroyl glutamate, 7 to 25 wt % of said (B) sodium cocoyl glycinate, and 1 to 5 wt % of said (C) potassium cocoyl glycinate with respect to a total weight of the cleansing foam cosmetic composition are included.

3. The composition of claim 2, wherein a weight ratio of (A) sodium lauroyl glutamate, (B) sodium cocoyl glycinate, and (C) potassium cocoyl glycinate is selected within the range of 7:7:1 to 13:13:1.4.

4. The composition of claim 3, wherein the weight ratio of (A) sodium lauroyl glutamate, (B) sodium cocoyl glycinate, and (C) potassium cocoyl glycinate is 10:10:1.4.

5. The composition of claim 1, further comprising water, an antioxidant, and a moisturizing agent.

6. The composition of claim 5, wherein the moisturizing agent is any one or more selected from the group consisting of glycerin, diglycerin, 1,3-butylene glycol, ethylene glycol, propylene glycol, dipropylene glycol, sorbitol, maltitol, 1,2-pentanediol, and 1,2-hexanediol.

7. The composition of claim 1, wherein the composition is a cream state or a paste state.

8. The composition of claim 2, wherein the composition is a cream state or a paste state.

9. The composition of claim 3, wherein the composition is a cream state or a paste state.

10. The composition of claim 4, wherein the composition is a cream state or a paste state.

11. The composition of claim 5, wherein the composition is a cream state or a paste state.

12. The composition of claim 6, wherein the composition is a cream state or a paste state.

* * * * *